United States Patent [19]

Sigwart et al.

[11] Patent Number: 6,002,027
[45] Date of Patent: Dec. 14, 1999

[54] PREPARATION OF 1,2-BUTYLENE OXIDE

[75] Inventors: Christoph Sigwart, Schriesheim; Franz Josef Bröcker, Ludwigshafen; Rolf Fischer, Heidelberg; Peter Lingelbach, Mutterstadt, all of Germany

[73] Assignee: BASF Aktiengesellschaft, Ludwigshafen, Germany

[21] Appl. No.: 09/046,124

[22] Filed: Mar. 23, 1998

Related U.S. Application Data

[62] Division of application No. 08/704,733, filed as application No. PCT/EP95/00656, Feb. 23, 1995, Pat. No. 5,869,707.

[30] Foreign Application Priority Data

Mar. 7, 1994 [DE] Germany .............................. 44 07 486

[51] Int. Cl.$^6$ ............................. C07D 301/02; C07C 5/03
[52] U.S. Cl. .......................... 549/540; 549/513; 585/273
[58] Field of Search ..................................... 549/540, 513; 585/273

[56] References Cited

U.S. PATENT DOCUMENTS 5,063,194  11/1991  Broecker et al. ....................... 502/314
5,117,013   5/1992  Falling ................................... 549/540

*Primary Examiner*—John Kight
*Assistant Examiner*—Charanjit S. Aulakh
*Attorney, Agent, or Firm*—Keil & Weinkauf

[57] ABSTRACT

A process for preparing 1,2-butylene oxide by catalytic hydrogenation of vinyloxirane over a heterogeneous catalyst comprises using a catalyst comprising an element of subgroup I, VII or VIII of the periodic table, or mixtures of a plurality of these elements, in the presence or absence of one or more promoter elements, these elements and promoters having been applied by means of a vacuum vapor deposition technique to a support of metal foil or metal wire fabric.

20 Claims, No Drawings

PREPARATION OF 1,2-BUTYLENE OXIDE

This is a Divisional Application of application Ser. No. 08/704,733, filed on Sep. 09, 1996, now U.S. Pat. No. 5,869,707, which is a 371 of PCT/EP95/00656 filed Feb. 23, 1995.

DESCRIPTION

The present invention relates to a process for preparing 1,2-butylene oxide by catalytic hydrogenation of vinyloxirane over a heterogeneous catalyst.

The catalytic hydrogenation of vinyloxirane is known.

According to U.S. Pat. No. 2,561,984, the hydrogenation of vinyloxirane in ethanol over a palladium/activated carbon catalyst at 25° C./2 bar gives n-butyraldehyde as main product after a reaction time of 3 hours. In contrast, Raney nickel as catalyst results in formation of mainly n-butanol at 25° C. and 2 bar after a reaction time of 1.5 hours. Nothing is recorded about the formation of butylene oxide.

A paper by Aizikovich et al. (J. Gen. Chem. USSR, 28 (1958) 3076) describes the catalytic hydrogenation of vinyloxirane in methanol or ethanol over platinum, palladium and Raney nickel catalysts. A supported palladium catalyst (1.8% by weight of palladium on calcium carbonate) results in formation of mainly n-butanol at 15° C./1 bar. In this document, the most important intermediate in the hydrogenation is regarded as crotyl alcohol, although the formation of n-butyraldehyde is also observed. In this paper too, there is no reference to the formation of butylene oxide.

In U.S. Pat. No. 5,077,418 and U.S. Pat. No. 5,117,013 it is reported that the hydrogenation of vinyloxirane solutions over palladium-containing catalysts gives n-butyraldehyde as main product. Thus, hydrogenation of vinyloxirane together with tetrahydrofuran as solvent over a palladium/ activated carbon catalyst (5% by weight of palladium on activated carbon) at from 50 to 55° C. and a pressure of 3.5 bar gives, after a reaction time of 3 hours, a hydrogenation product containing 55% of n-butyraldehyde, only 27% of butylene oxide and 9% of n-butanol.

If the hydrogenation is carried out over supported catalysts containing palladium on aluminum oxide (5% Pd/$Al_2O_3$), only traces of butylene oxide are formed after a reaction time of 6 hours at from 25 to 55° C. and a pressure of 3.5 bar or after a reaction time of 4 hours at 100° C. and a pressure of 20.7 bar. Quantitative conversion gives n-butyraldehyde as main product at a selectivity of 87% or 78%.

In addition, the hydrogenation of vinyloxirane over Raney nickel as hydrogenation catalyst at 50° C. and 3.5 bar is described, with 58% of n-butanol being formed as main product. The yield of butylene oxide is, at 41%, low. In the hydrogenation of vinyloxirane over a supported platinum catalyst (1% by weight of Pt/$Al_2O_3$) at 100° C. and a hydrogen pressure of 20.7 bar, only 40% of butylene oxide together with 23% of n-butanol, 24% of various butenols, 5% of crotonaldehyde and 3% of n-butyraldehyde are found for complete conversion after a reaction time of 4.6 hours. Other platinum-containing catalysts give even lower butylene oxide yields.

Furthermore, U.S. Pat. No. 5,077,418 and U.S. Pat. No. 5,117,013 teach that high butylene oxide yields are only obtained using rhodium-containing catalysts. Various supported rhodium catalysts (5% by weight of rhodium an activated carbon; 5% by weight of rhodium on aluminum oxide), which have a high content of the expensive noble metal rhodium, or hydrated rhodium oxide ($Rh_2O_3 \cdot xH_2O$) give butylene oxide contents of 60–93% in the hydrogenation of vinyloxirane solutions. A disadvantage of this process is the low space-time yield based on the amount of rhodium used. Thus, the space-time yield in Example 2 of U.S. Pat. No. 5,117,013 is only 119 kg of 1,2-butylene oxide/kg Rh*h.

Neftekhimiya 33 (1993) 131 describes the hydrogenation of vinyloxirane over catalysts containing nickel, palladium and copper. Using Raney nickel or nickel on kieselguhr as catalyst, the hydrogenation proceeds primarily with opening of the epoxide ring which leads to the predominant formation of 1-butenols and n-butanol. The yields of butylene oxide are low. For example, Raney nickel with methanol as solvent at 40° C./60 bar hydrogen pressure gives, after a reaction time of 20 min at a conversion of 94%, a reaction product which, based on reacted vinyloxirane, contains 89% of butenols, 8% of n-butanol and only 2% of butylene oxide. The hydrogenation of vinyloxirane in methanol at 20° C./60 bar $H_2$ using freshly prepared Raney nickel also gives, after a reaction time of 3 minutes at a conversion of 94%, only 9% of butylene oxide in addition to 79% of n-butanol and 6% of butenol. A hydrogenation experiment in methanol at 20° C./60 bar hydrogen pressure over a Raney nickel catalyst pretreated with isopropanol, nicotinic acid, pyridine and morpholine results, at 89% conversion, in the highest butylene oxide selectivity achievable using a nickel-containing catalyst, viz. 37%. At the same time, butenols and n-butanol are obtained in a selectivity of 56% and 9% respectively.

With palladium-containing catalysts, higher butylene oxide selectivities are achieved in the hydrogenation of vinyloxirane compared with the experiments using nickel-containing catalysts. For example, a palladium/activated carbon catalyst gives, without use of a solvent at 15° C./60 bar hydrogen pressure after a reaction time of 13 minutes at 61% conversion, 81% of butylene oxide based on converted vinyloxirane. On the other hand, under the same reaction conditions using methanol as solvent, a butylene oxide selectivity of only 53% is obtained at a conversion of 86%, with 13% of butanol and 18% of butenols being formed. A disadvantage of this process is that a high selectivity for the formation of 1,2-butylene oxide is achieved only at a relatively low partial conversion of the vinyloxirane. Since vinyloxirane and 1,2-butylene oxide are very difficult to separate from one another by distillation, this process is thus of no industrial importance. Palladium catalysts based on a polymer give, at a conversion of 68%, maximum butylene oxide selectivities of 60%, with butenol and n-butanol being formed in a selectivity of 18% and 4% respectively.

With copper-containing catalysts, a lower hydrogenation activity and resinification of the hydrogenation product is observed, making this process industrially impractical. At reaction temperatures of 60–100° C., 60 bar $H_2$ and 30% by weight of catalyst, a vinyloxirane conversion of 50% and a butylene oxide selectivity of 70% are achieved after a reaction time of 3 hours.

It is an object of the present invention to provide an economical process for preparing 1,2-butylene oxide from vinyloxirane in high yield and selectivity. It is a further object to provide catalysts for this purpose which achieve that object and, compared with prior art catalysts, require significantly lower amounts of costly noble metals, especially rhodium or palladium, as catalyst component.

We have found that these objects are achieved by a process for preparing 1,2-butylene oxide by catalytic hydrogenation of vinyl-oxirane over a heterogeneous catalyst, which comprises using a catalyst comprising an element of subgroup I, VII or VIII of the Periodic Table, or mixtures of these elements, in the presence or absence of one or more promoter elements, these elements and promoters having been applied by means of a vacuum vapor deposition technique to a support of metal foil or metal wire fabric.

The process of the present invention suprisingly makes it possible to hydrogenate the double bond of vinyloxirane (I) selectively according to equation (1)

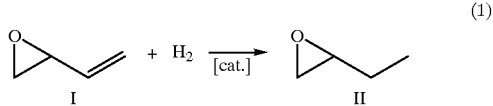

without the sensitive epoxide ring being hydrogenolytically cleaved to any appreciable extent and without appreciable occurrence of other secondary reactions, for example isomerizations of vinyloxirane, for example to butyraldehyde or crotonaldehyde, which are subsequently hydrogenated to butanol and crotyl alcohol. Since the catalysts used according to the present invention have a very low content of the catalytically active, but very costly, noble metals, such as rhodium and palladium, compared with other, prior art catalysts, the process of the present invention provides a very economical way of preparing 1,2-butylene oxide (II) selectively.

The catalysts used according to the present invention are prepared by using a vacuum vapor deposition technique to apply the elements of subgroup I, VII or VIII of the periodic table, especially copper, silver, gold, rhenium, ruthenium, cobalt, rhodium, nickel, palladium or platinum or mixtures thereof, to a metal support which may be in the form of metal foil or metal wire fabric.

As well as the elements of subgroup I, VII or VIII of the periodic table, it is additionally possible to apply promoter and/or stabilizer elements to the metal support. Such elements are for example the elements of main group IV and of subgroups II and IV of the periodic table, especially lead, tin, silicon, zinc, cadmium, titanium and zirconium. These elements, herein simply referred to as promoters, can be applied to the metal support by vacuum vapor deposition techniques individually or mixed with other promoter elements together with one or more of the elements of subgroup I, VII or VIII of the periodic table.

The catalytically active metals of subgroup I, VII or VIII of the periodic table, or mixtures thereof, are generally applied to the metal support, with or without one or more of the promoter elements, in an amount of in general from 1 to 300 mg per $m^2$ of area of the metallic support material, preferably in an amount of from 20 to 200 mg per $m^2$ of area, especially in an amount from 40 to 100 mg per $m^2$ of area of the metallic support material. The promoter elements of main group IV or of subgroup II or IV of the periodic table, or mixtures thereof, are generally deposited on the metal support in an amount of in each case from 1 to 300 mg per $m^2$ of area of the metallic support material, preferably in an amount of from 20 to 200 mg per $m^2$ of area, especially in an amount from 40 to 100 mg per $m^2$ of area of the metallic support material. The individual catalyst components—catalytically active elements and promoter elements—can be deposited simultaneously or successively.

The support materials used can be metal foils or wire fabrics woven from various, weavable metal wires, such as iron, spring steel, copper, brass, phosphorus bronze, pure nickel, Monel, aluminum, silver, nickel brass, nickel, chromium nickel, chromium steel, chromium nickel steel and also titanium. Particularly highly suitable support materials for the process of the present invention are metal foils and especially metal wire fabrics in the materials bearing the material numbers 1.4767 (alloyed high-grade steel, stainless, containing 19.0/22.0% by weight chromium, 4.0/5.5% by weight aluminum, $\leq 0.10\%$ by weight carbon, $\leq 1.0\%$ by weight silicium, $\leq 1.0\%$ by weight manganese, $\leq 0.45\%$ by weight phosphor and $\leq 0.030\%$ by weight sulfur), 1.4401 (alloyed high-grade steel, stainless, containing 16.5/18.5% by weight chromium, 2.0/2.5% by weight molybdenum, 10.5/13.5% by weight nickel, $\leq 0.07\%$ by weight carbon, $\leq 1.0\%$ by weight silicium, $\leq 2.0\%$ by weight manganese, $\leq 0.45\%$ by weight phosphor and $\leq 0.030\%$ by weight sulfur) and 1.4301 (alloyed high-grade steel, stainless, containing 17.0/19.0% by weight chromium, 8.5/10.5% by weight nickel, $\leq 0.07\%$ by weight carbon, $\leq 1.0\%$ by weight silicium, $\leq 2.0\%$ by weight manganese, $\leq 0.45\%$ by weight phosphor and $\leq 0.030\%$ by weight sulfur). The designation of these materials with the abovementioned material numbers in accordance with the material numbers specified in Stahleisenliste, published by Verein Deutscher Eisenhuttenleute; 8th edition, pages 87, 89 and 106, Verlag Stahleisen mbH, Dusseldorf 1990. The material bearing material number 1.4767 is also known as Kanthal.

Suitable support material for the catalysts which are usable in the process of the present invention include, as well as metal foils, metal wire wovens in different constructions, for example plain wovens, twill wovens, galloon wovens, five end satin wovens including fancy weaves. Other advantageous support materials include shaped articles formed from metal foils, metal wire wovens or wire knit, for example spirals, Raschig rings or monoliths.

These metal supports are advantageously subjected to an oxidative tempering prior to their coating with the catalytically active metals and any promoters. The oxidative tempering of these supports involves heating them, preferably in air, to temperatures of from 600 to 1100° C., preferably to temperatures of from 750 to 1000° C.

The metal foil or wire woven, optionally following a preceding oxidative tempering, is coated by means of a vacuum vapor deposition technique with thin films of the catalytically active metals and optionally the promoters. Thin films have a thickness ranging from a few angstrom to not more than a few micrometers. The film thickness can be measured by means of a vibrating quartz crystal.

Suitable vacuum vapor deposition techniques include for example thermal vaporization, flash vaporization, cathode sputtering and also the combination of thermal vaporization and cathode sputtering. Thermal vaporization can be effected by direct or indirect electric heating. Another possibility is electron beam vaporization. It involves using an electron beam to heat the surface of the substance to be vaporized, in a water-cooled crucible, to such an extent that even high melting metals and dielectrics can be vaporized.

These methods provide an optimum way of coating the catalyst support specifically with the catalytically active elements and any promoters. Alloys are preferably applied by flash vaporization.

The metal support can be vaporized batchwise or continuously in a vacuum vapor depositor, for example by using an electron beam, in a vacuum of from $10^{-2}$ to $10^{-10}$, preferably from $10^{-4}$ to $10^8$, Torr to heat the active component to be applied to such an extent that the metal vaporizes out of the water-cooled crucible and deposits on the support. The support material is advantageously arranged in such a way as to maximize the proportion of the vapor stream which condenses on the support. The metal supports can be coated continuously by means of a built-in winding machine. Wire knits, for example Raschig rings formed from fine wires, can be introduced for example into a rotary drum basket for loose stock and vapor-coated therein.

The vacuum vapor deposition techniques usable for preparing the catalysts usable according to the present invention are themselves not part of the subject-matter of the present invention. As regards the details of the procedure of coating the metal supports with catalytically active metals and promoters reference is therefore made to handbooks, for example Maissel, Glang, Handbook of Thin Film Technology, McGraw Hill, New York, 1970, and Vossen, Kern, Thin Film Processes, Academic Press, New York, 1978 or U.S. Pat. No. 4,686,202.

After the coating has been carried out, it can be advantageous to subject the coated support material to a thermal conditioning treatment by treating it, preferably in the presence of air or oxygen, at temperatures of generally from 20 to 800° C., preferably from 25 to 70° C., for a period of generally from 0.5 to 2 h. Unless already coated in that form, the metal foils or metal wire wovens can also be formed into shaped articles, such as Raschig rings, spirals and monoliths, after the coating and conditioning, if desired.

The catalysts thus prepared can be used directly in the process of the present invention, but advantageously they are reduced before use in the process of the present invention, generally ith hydrogen or hydrogen-containing gases at temperatures of typically from 50 to 300° C., preferably from 80 to 250° C. The reduction is generally carried on until the formation of water has ceased.

The process of the present invention involves hydrogenating vinyloxirane, or solutions of vinyloxirane in a solvent which is inert under the reaction conditions, in the presence of the catalysts to be used according to the present invention at temperatures of from generally 0 to 200° C., preferably from 10 to 130° C., especially from 20 to 100° C., and particularly preferably at from 40 to 100° C., at a pressure of generally from 1 to 300 bar, preferably from 1 to 100 bar and particularly preferably from 1 to 50 bar.

The process of the invention can be carried out without a solvent or preferably in the presence of a solvent which is inert under the reaction conditions. Such solvents include for example ethers such as tetrahydrofuran, dioxane, methyl tert-butyl ether, di-n-butyl ether, dimethoxyethane and diisopropyl ether, alcohols such as methanol, ethanol, propanol, isopropanol, n-butanol, isobutanol and tert-butanol, $C_2$–$C_4$-glycols, hydrocarbons such as petroleum ether, benzene, toluene and xylene, and N-alkyllactams such as N-methylpyrrolidone or N-octylpyrrolidone.

The process of the present invention can be carried out both continuously and batchwise, in the gas phase or in the liquid phase. A continuous process can be carried out with advantage for example in tubular reactors in which the catalyst is preferably arranged in the form of monoliths over which the reaction mixture is passed in the upflow or downflow mode. In the case of a batchwise process, not only simple stirred reactors or advantageously loop reactors can be used. When loop reactors are used, the catalyst is advantageously disposed in the reactor in the form of monoliths or Raschig rings.

The reaction mixture can be worked up for 1,2-butylene oxide in a conventional manner, for example by distillation.

The vinyloxirane required as starting material can be prepared for example by the process of U.S. Pat. No. 4 897 498 by partial oxidation of 1,3-butadiene over silver catalysts. 1,2-Butylene oxide is used, for example, as a motor fuel additive or as a stabilizer of chlorinated hydrocarbons.

EXAMPLES

In all examples the vacuum vapor deposition machine used was a commercially available electron beam vapor depositor from Balzers AG, Balzers (Duchy of Liechtenstein).

Example 1

A plain woven wire fabric in material No. 1.4767, having a mesh size of 0.18 mm and a wire diameter of 0.112 mm, was heated in air at 950° C. for 5 h. The support woven thus pretreated was then coated with palladium in an electron beam vapor depositor. The amount of palladium deposited was 92 mg of palladium per $m^2$ of area of the woven. The catalyst woven thus prepared was conditioned in air at 25° C. and then used to produce 5 ×5 mm Raschig rings. In a 50 ml capacity autoclave, the solution to be hydrogenated, comprising 2.5 g of vinyloxirane and 22.5 g of tetrahydrofuran, was admixed with 20 $cm^2$ of palladium-coated catalyst woven in the form of Raschig rings and hydrogenated with hydrogen at 50° C. and 40 bar over 6 h with stirring. The amount of palladium used was thus 184 μg. Conversion was 100%, and the composition of the product was 78.4 mol% of butylene oxide, 2.7 mol% of n-butyraldehyde and 3.3 mol% of n-butanol.

Example 2

The same wire woven as in Example 1 was heated to 1000° C. in air for 5 h. After cooling, this support material was coated in the same vacuum vapor depositor as in Example 1 successively with 92 mg of palladium per $m^2$ of area of the support and 21.3 mg of lead per $m^2$ of support area. To condition the catalyst, the coated woven was tempered in air at 600° C. for 0.5 h. The woven was then shaped into 5×5 mm Raschig rings, which were activated in a quartz tube at 200° C. with hydrogen at atmospheric pressure and cooled down under a nitrogen atmosphere. In this form, 15 $cm^2$ of the catalyst were used for the hydrogenation of 2.5 g of vinyloxirane in 22.5 g of tetrahydrofuran. The hydrogenation was carried out as described in Example 1. Conversion was 100%, and the composition of the product was 83.9 mol% of 1,2-butylene oxide, 1.9 mol% of n-butyraldehyde and 2.4 mol% of n-butanol.

Example 3

By the procedure of Example 1 the same wire woven was heated in air at 1000° C. for 5 h and then vacuum coated in succession with 92 mg of palladium per $m^2$ of support area and 20.2 mg of gold per $m^2$ of support area and conditioned. After 5×5 mm Raschig rings had been formed, 18.75 $cm^2$ of this catalyst were introduced into an autoclave and the hydrogenation of 2.5 g of vinyloxirane in 22.5 g of tetrahydrofuran was carried out at 50° C. and 40 bar hydrogen pressure for 8 h. Conversion was 100%, and the composition of the product was 89.1 mol% of 1,2-butylene oxide, 1.7 mol% of n-butyraldehyde and 1.0 mol% of n-butanol.

Example 4

The same wire woven as in Examples 1 to 3 was heated at 950° C. for 5 h and, after cooling down, vacuum coated with 46 mg of palladium per $m^2$ of area and 6.1 mg of silicon per $m^2$ of area and conditioned. After the catalyst woven had been shaped into 5×5 mm Raschig rings, 20 $cm^2$ of this catalyst were used for the hydrogenation run, which was carried out under the same reaction conditions as described in Example 3. Conversion was 97.7%, and the composition of the product was 85.3 mol% of 1,2-butylene oxide, 1.2 mol% of n-butyraldehyde and 1.3 mol% of n-butanol.

Example 5

The wire woven of Examples 1 to 4 was heated at 900° C. for 5 h and then coated in the vacuum vapor depositor in succession with 46 mg of palladium per $m^2$ of area and 19.7 mg of zirconiun per $m^2$ of area and conditioned as in Example 1. The catalyst fabric was shaped into 5×5 mm Raschig rings and in this form 20.0 $cm^2$ of catalyst were introduced into the hydrogenation autoclave. Then 2.5 g of vinyloxirane in 22.5 g of tetrahydrofuran were hydrogenated at 50° C. and 40 bar hydrogen pressure for 4 h. Conversion was quantitative, and the composition of the product was 84.6 mol% of 1,2-butylene oxide, 1.6 mol% of n-butyraldehyde and 1.3 mol% of n-butanol.

Example 6

The same wire woven as in Examples 1 to 5 was following the same pretreatment as in Example 5 vacuum coated in succession with 46 mg of palladium per $m^2$ of area and 10.4 mg of titanium per $m^2$ of area and conditioned as in Example 1. The resulting catalyst fabric was shaped into 5×5 mm Raschig rings and 21.25 $cm^2$ thereof were used for the autoclave run. It was carried out under the same reaction conditions as described in Example 5. Conversion was complete, and the composition of the product was 82.4 mol% of butylene oxide, 1.6 mol% of n-butyraldehyde and 2.1 mol% of n-butanol.

Example 7

The same wire woven as in Examples 1 to 6 was heated at 1000° C. in air for 5 h. Nickel was then applied in the vacuum vapor depositor in an amount of 66 mg of nickel per $m^2$ of area, followed by conditioning as in Example 1. This catalyst fabric was used to make into 5×5 mm Raschig rings, which were activated with hydrogen at 230° C. as described in Example 2. 22.5 $cm^2$ of the activated catalyst were used for the hydrogenation run which was carried out under the same reaction conditions as described in Example 3. Conversion was 94.8%, and the composition of the product was 80.8 mol% of 1,2-butylene oxide, 1.7 mol% of n-butyraldehyde and 4.1 mol% of n-butanol.

Example 8

The same support woven as in Examples 1 to 7 was heated at 950° C. in air for 5 h. After cooling, it was vacuum coated in succession with 66 mg of nickel per $m^2$ of area and 92 mg of palladium per m2 of area and conditioned as in Example 1. After the catalyst woven had been shaped into 5×5 mm Raschig rings, the catalyst was activated with hydrogen as described in Example 7. 21.25 $cm^2$ of the activated catalyst were used for the hydrogenation. Under the same reaction conditions as described in Example 1, conversion was complete; and the composition of the product was 84.0 mol% of butylene oxide, 2.3 mol% of n-butyraldehyde and 3.5 mol% of n-butanol.

Example 9

The same woven as in Examples 1 to 8 was heated at 950° C. in air for 5 h and, after cooling, coated in the vacuum vapor depositor in succession with 66 mg of nickel per $m^2$ of area and 16.1 mg of rhenium per $m^2$ of area. To condition the coated woven, it was heated up to 600° C. in air for 2 h and tempered at that temperature for 0.5 h. Then 5×5 mm Raschig rings were fabricated from the catalyst woven and 21.25 $cm^2$ of the catalyst woven were used for the hydrogenation run. Under the same reaction conditions as described in Example 3 conversion was quantitative and the composition of the product was 82.6 mol% of 1,2-butylene oxide, 1.9 mol% of n-butyraldehyde and 4.3 mol% of n-butanol.

Example 10

The woven of Examples 1 to 9 was heated at 1000° C. for 5 h and, after cooling, vacuum coated in succession with 66 mg of nickel per $m^2$ of area and 16.1 mg of palladium per $m^2$ of area and 16.1 mg of rhenium per $m^2$ of area. The woven was then heated to 600° C. in air over 2 h and tempered at that temperature for 0.5 h. Following the customary preparation of 5×5 mm Raschig rings, the catalyst was activated under atmospheric pressure with hydrogen at 200° C. in a quartz tube. 21.25 $cm^2$ of the activated catalyst woven were used for the hydrogenation run, which was carried out under the same reaction conditions as described in Example 3. Conversion was 97.2% and the composition of the product was 82.2 mol% of 1,2-butylene oxide, 1.7 mol% of n-butyraldehyde and 4.6 mol% of n-butanol.

Example 11

The same woven as in-the preceding examples was heated at 1000° C. in air for 5 h. The support material thus pretreated was vacuum coated with 88 mg of rhodium per $m^2$ of area. The coated fabric was then conditioned as in Example 1. The resulting catalyst woven was used to fabricate 5×5 mm Raschig rings, and a catalyst woven quantity of 21.25 $cm^2$ was used for the hydrogenation of vinyloxirane carried out under the same reaction conditions as described in Example 3. Conversion was complete and the composition of the product was 86.0 mol% of 1,2-butylene oxide, 4.0 mol% of n-butyraldehyde and 4.5 mol% of n-butanol. The space-time yield based on the amount of rhodium used was 1,437 kg of 1,2-butylene oxide/kg of Rh.h.

Example 12

Woven fabric heated at 1000° C. in air for 5 h as per the preceding examples was coated in succession in the electron beam vapor depositor with 24 mg of rhodium per $m^2$ of area and 46 mg of palladium per $m^2$ of area. For conditioning, the resulting material was heated over 1 h to 500° C. in air and tempered at that temperature for 1 h. After preparation of 5×5 mm Raschig rings from the resulting catalyst fabric, 21.25 $cm^2$ were used for the hydrogenation run. The hydrogenation of 2.5 g of vinyloxirane and 22.5 g of tetrahydrofuran at 50° C. and 40 bar hydrogen pressure for 2 h proceeded with quantitative conversion and the composition of the product was 90.1 mol% of 1,2-butylene oxide, 1.8 mol% of n-butyraldehyde and 2.5 mol% of n-butanol.

Examples 13 to 17

20 $cm^2$ of the palladium-coated catalyst woven of Example 1 were used for hydrogenation runs for hydrogenating 2.5 g of vinyloxirane in 22.5 g of different solvents at 50° C. and 40 bar hydrogen pressure. The compositions of the reactor effluents are shown in the table.

TABLE

| Ex. | Solvent | Reaction time | \multicolumn{4}{c}{Composition of reactor effluent} |
|-----|---------|------|------|------|------|------|
|     |         |      | VO   | BO   | n-BA | n-BuOH |
| 13  | MTBE          | 1 h | — | 83.4 | 2.3 | 1.7 |
| 14  | Di-n-butyl ether | 2 h | — | 78.9 | 0.9 | 1.0 |
| 15  | Methanol      | 2 h | — | 78.8 | 2.6 | 7.2 |
| 16  | Ethanol       | 2 h | — | 75.1 | 1.0 | 2.5 |
| 17  | Toluene       | 2 h | — | 77.0 | 1.8 | 2.5 |

VO = Vinyloxirane
BO = 1,2-Butylene oxide
n-BA = n-Butyraldehyde
n-BuOH = n-Butanol
MTBE = Methyl tert-butyl ether Example 18

Plain woven wire fabric in material No. 1.4301, having a mesh size of 0.125 mm and a wire diameter of 0.100 mm, was heated at 800° C. in air for 3 h. The support material thus prepared was then coated with palladium in an electron beam vapor depositor. The amount of palladium applied was 92 mg of palladium per m² of area of support fabric. The catalyst thus prepared was used to make 5×5 mm Raschig rings. 2.5 g of vinyloxirane and 22.5 g of tetrahydrofuran were introduced into a 50 ml capacity autoclave, complemented with 21.25 cm² of the shaped catalyst fabric, and hydrogenated at 50° C. and 40 bar hydrogen pressure for 7 h with stirring. Conversion was 97.7% and the composition of the product was 81.0 mol% of butylene oxide, 1.6 mol% of n-butyraldehyde and 4.6 mol% of n-butanol, based on converted vinyloxirane.

Example 19

Plain woven wire fabric in the material of material No. 1.4401, mesh size 0.160 mm, wire diameter 0.100 mm, was heated at 850° C. in air for 3 h, then vacuum coated with 92 mg of palladium per m² of area and conditioned as in Example 1. 21.25 cm² of this catalyst fabric in the form of Raschig rings were used to hydrogenate vinyloxirane and tetrahydrofuran similarly to Example 18. Conversion was 99.5%, and the composition of the reactor effluent was 79.3 mol% of 1,2-butylene oxide, 1.9 mol% of n-butyraldehyde and 3.4 mol% of n-butanol.

Example 20

Wire woven in material of material No. 1.4767 was pretreated as described in Example 1, vacuum coated with 161.2 mg of rhenium per m² of area of fabric and conditioned as in Example 1. 42.5 cm² of the catalyst fabric thus prepared in the form of 5×5 mm Raschig rings were used to carry out the vinyloxirane hydrogenation of Example 18 at 95° C. and 40 bar hydrogen pressure. Following a reaction time of 8 h conversion was 29.3% and the composition of the reaction mixture was 76.0 mol% of 1,2-butylene oxide, 4.4 mol% of n-butyraldehyde and 4.7 mol% of n-butanol, based on converted vinyloxirane.

Example 21

The wire woven in of Example 1 was heated at 950° C. in air for 5 h, then vacuum coated with 91.2 mg of ruthenium per m² of area of fabric and conditioned as in Example 1. 42.5 cm² of this catalyst fabric in the form of 5×5 mm Raschig rings were used in the hydrogenation. The hydrogenation was carried out at 95° C. and a hydrogen pressure of 40 bar. Conversion was 31.3% after 4 h and the composition of the product was 83.4 mol% of 1,2-butylene oxide, 3.1 mol% of n-butyraldehyde and 2.5 mol% of n-butanol, based on converted vinyloxirane.

Example 22

The catalyst fabric pretreated as in Example 1 was coated with 166.4 mg of cobalt per m² of fabric by vapor deposition and conditioned as in Example 1. 21.25 cm² of this catalyst fabric were used in the form of Raschig rings (5×5 mm) for the hydrogenation of vinyloxirane. The hydrogenation was carried out at 50° C. and 40 bar hydrogen pressure. Conversion was 40% after 24 h and the composition of the reactor effluent was 83.2 mol% of 1,2-butylene oxide, 1.8 mol% of n-butyraldehyde and 2.6 mol% of n-butanol, based on converted vinyloxirane.

Example 23

The metal woven pretreated as in Example 1 was coated with 67 mg of copper per m² of area of fabric by vacuum vapor deposition and conditioned as in Example 1. 42.5 cm² of this catalyst woven were used in the form of Raschig rings (5×5 mm) for the hydrogenation of vinyloxirane at 95° C. and 40 bar hydrogen pressure. Conversion after 8 h reaction time was 18%, and 89.6 mol% of 1,2-butylene oxide was formed, based on converted vinyloxirane.

Example 24

The metal woven pretreated as in Example 1 was coated with 160 mg of platinum per m² of area of fabric by vapor deposition and conditioned as in Example 1. 21.25 cm² of this catalyst in the form of Raschig rings (5×5 mm) were used for the hydrogenation of vinyloxirane at 50° C. and 40 bar hydrogen pressure. Conversion was 85.4% after 24 h and the reaction mixture contained 64.4 mol% of 1,2-butylene oxide, 3.6 mol% of n-butyraldehyde and 16.4 mol% of n-butanol, based on converted vinyloxirane.

Example 25

The catalyst woven of Example 5 was made into Raschig rings and used in an amount of 40.0 cm² for the hydrogenation run. The hydrogenation of 10.0 g of vinyloxirane at 50° C. and 40 bar hydrogen pressure in the absence of a solvent proceeded with quantitative conversion after a reaction time of 7 h, when the reaction mixture contained 83.9 mol% of 1,2-butylene oxide, 1.0 mol% of n-butyraldehyde and 0.8 mol% of n-butanol. The space-time yield, based on the amount of palladium used, was 6,522 kg of 1,2-butylene oxide/kg of Pd.h.

We claim:

1. A process for preparing 1,2-butylene oxide by catalytic hydrogenation of vinyloxirane over a heterogeneous catalyst, wherein the catalyst comprises
   a) rhodium alone or in combination with a further element of subgroup I, VII or VIII of the periodic table, or mixtures of a plurality of these elements, and
   b) optionally one or more promoter elements, and wherein the elements and promoters have been applied by means of a vacuum vapor deposition technique to a support of metal foil or metal wire woven.

2. The process defined in claim 1, wherein the catalyst comprises one or more elements of main group IV or of subgroup II or IV of the periodic table as promoters.

3. The process defined in claim 1, wherein the metal foil or metal wire woven support is formed from materials bearing the material numbers 1.4767, 1.4401 or 1.4301.

4. The process defined in claim 1, wherein the support is heated in air at from 600 to 1100° C. before the catalytically active elements are applied.

5. The process defined in claim 1, wherein the catalyst comprises rhodium alone or in combination with one or more further elements of subgroup I, VII or VIII of the periodic table applied to the metal support in an amount of in each case from 1 to 300 mg/m$^2$ of area of the support.

6. The process defined in claim 1, wherein the catalyst, as well as rhodium alone or in combination with the elements of subgroup I, VII or VIII of the periodic table, further comprises promoter elements, these promoter elements having been applied to the metal support in an amount of in each case from 1 to 300 mg/m$^2$ of area of the support.

7. The process defined in claim 1, wherein the catalyst has been conditioned in air at from 20 to 8000° C. after the catalytically active elements were applied.

8. The process defined in claim 1, wherein the catalyst was reduced with hydrogen at from 20 to 300° C. before use.

9. A process for preparing 1,2-butylene oxide by catalytic hydrogenation of vinyloxirane over a heterogeneous catalyst, wherein the catalyst comprises
   a) rhodium alone or in combination with one or more further elements of subgroup I, VII or VIII of the Periodic Table, selected from the group consisting of copper, silver, gold, rhenium, ruthenium, cobalt, nickel, palladium and platin, and
   b) optionally one or more promoter elements, and wherein the elements and promoters have been applied by means of a vacuum vapor deposition technique to a support of metal foil or metal wire woven.

10. The process defined in claim 9, wherein the catalyst comprises one or more elements of main group IV or of subgroup II or IV of the Periodic Table as promoters.

11. The process defined in claim 9, wherein the metal foil or metal wire woven support is formed from materials bearing the material numbers 1.4767, 1.4401 or 1.4301.

12. The process defined in claim 9, wherein the catalyst comprises rhodium alone or in combination with one or more further elements of subgroup I, VII or VIII of the Periodic Table applied to the metal support in an amount of in each case from 1 to 300 mg/m$^2$ of area of the support.

13. The process defined in claim 9, wherein the catalyst, as well as rhodium alone or in combination with the elements of subgroup I, VII or VIII of the Periodic Table, further comprises promoter elements, these promoter elements having been applied to the metal support in an amount of in each case from 1 to 300 mg/m$^2$ of area of the support.

14. The process defined in claim 9, wherein the catalyst was reduced with hydrogen at from 20 to 300° C. before use.

15. A process for preparing 1,2-butylene oxide by catalytic hydrogenation of vinyloxirane over a heterogeneous catalyst, wherein the catalyst comprises
   a) rhodium alone or in combination with one or more further elements of subgroup VIII of the Periodic Table, and
   b) optionally one or more promoter elements, and wherein the elements and promoters have been applied by means of a vacuum vapor deposition technique to a support of metal foil or metal wire woven.

16. The process defined in claim 15, wherein the catalyst comprises one or more elements of main group IV or of subgroup II or IV of the Periodic Table as promoters.

17. The process defined in claim 15, wherein the metal foil or metal wire woven support is formed from materials bearing the material numbers 1.4767, 1.4401 or 1.4301.

18. The process defined in claim 15, wherein the catalyst comprises rhodium alone or in combination with one or more further elements of subgroup VIII of the Periodic Table applied to the metal support in an amount of in each case from 1 to 300 mg/m$^2$ of area of the support.

19. The process defined in claim 15, wherein the catalyst, as well as rhodium alone or in combination with the elements of subgroup VIII of the Periodic Table, further comprises promoter elements, these promoter elements having been applied to the metal support in an amount of in each case from 1 to 300 mg/m$^2$ of area of the support.

20. The process defined in claim 15, wherein the catalyst was reduced with hydrogen at from 20 to 300° C. before use.

* * * * *

UNITED STATES PATENT AND TRADEMARK OFFICE
CERTIFICATE OF CORRECTION

PATENT NO.: 6,002,027

DATED: December 14, 1999

INVENTOR(S): SIGWART et al.

It is certified that error appears in the above-identified patent and that said Letters Patent is hereby corrected as shown below:

Col. 11, claim 7, line 16, "8000°C" should be --800°C--.

Signed and Sealed this

Twentieth Day of June, 2000

*Attest:*

*Attesting Officer*

Q. TODD DICKINSON

*Director of Patents and Trademarks*